(12) United States Patent
Niu et al.

(10) Patent No.: US 6,928,395 B2
(45) Date of Patent: Aug. 9, 2005

(54) METHOD AND SYSTEM FOR DYNAMIC LEARNING THROUGH A REGRESSION-BASED LIBRARY GENERATION PROCESS

(75) Inventors: Xinhui Niu, San Jose, CA (US); Nickhil Jakatdar, Los Altos, CA (US)

(73) Assignee: TImbre Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/856,183

(22) Filed: May 27, 2004

(65) Prior Publication Data

US 2004/0225477 A1 Nov. 11, 2004

Related U.S. Application Data

(62) Division of application No. 09/923,578, filed on Aug. 6, 2001, now Pat. No. 6,785,638.

(51) Int. Cl.[7] .................................................. G01J 4/00
(52) U.S. Cl. ........................ 702/189; 702/81; 702/159; 702/193; 702/123; 356/601; 356/625
(58) Field of Search ............................. 702/66, 67, 69, 702/70, 72, 74–76, 81, 84–86, 117–120, 123, 151, 159, 189, 193, FOR 104, FOR 117, FOR 114, FOR 108, FOR 110, FOR 135, FOR 136, FOR 137, FOR 148, FOR 155–FOR 157, FOR 159–FOR 160, FOR 165, FOR 170, FOR 171; 438/5–13, 800; 118/663, 675, 679; 356/629, 300, 326, 601, 625, 630, 634, 635, 636, 638, 639, 640, 902; 706/12, 20, 46, 934; 716/4

(56) References Cited

U.S. PATENT DOCUMENTS

| | | |
|---|---|---|
| 4,999,508 A | 3/1991 | Hyakumura |
| 5,365,340 A | 11/1994 | Ledger |
| 6,219,142 B1 | 4/2001 | Kane |
| 6,292,265 B1 | 9/2001 | Finarov et al. |
| 6,346,702 B1 | 2/2002 | Davis et al. |
| 6,383,824 B1 | 5/2002 | Lensing |
| 6,383,888 B1 | 5/2002 | Stirton |
| 6,433,871 B1 | 8/2002 | Lensing et al. |
| 6,451,700 B1 | 9/2002 | Stirton et al. |
| 6,458,605 B1 | 10/2002 | Stirton |
| 6,476,920 B1 | 11/2002 | Scheiner et al. |
| 6,479,309 B1 | 11/2002 | Wright |
| 6,609,086 B1 * | 8/2003 | Bao et al. .................. 702/189 |
| 6,768,983 B1 * | 7/2004 | Jakatdar et al. ............... 706/46 |
| 2002/0035455 A1 * | 3/2002 | Niu et al. ...................... 703/4 |
| 2002/0038196 A1 | 3/2002 | Johnson et al. |
| 2002/0113966 A1 | 8/2002 | Shchegrov et al. |
| 2002/0158193 A1 | 10/2002 | Sezginer et al. |
| 2004/0018653 A1 * | 1/2004 | Johnson et al. ............... 438/16 |
| 2004/0070772 A1 * | 4/2004 | Shchegrov et al. ......... 356/625 |
| 2004/0078108 A1 * | 4/2004 | Choo et al. ................. 700/121 |
| 2004/0141177 A1 * | 7/2004 | Zhao et al. ................. 356/369 |
| 2004/0167722 A1 * | 8/2004 | Johnson et al. ............. 702/208 |
| 2004/0184035 A1 * | 9/2004 | Li et al. ..................... 356/369 |

* cited by examiner

*Primary Examiner*—Marc S. Hoff
*Assistant Examiner*—Carol S. Tsai
(74) *Attorney, Agent, or Firm*—Morrison & Foerster LLP

(57) ABSTRACT

The present invention relates to a method and system for efficiently determining grating profiles using dynamic learning in a library generation process. The present invention also relates to a method and system for searching and matching trial grating profiles to determine shape, profile, and spectrum data information associated with an actual grating profile.

29 Claims, 14 Drawing Sheets

| Entry ID (602) | Shape - profile data (604) | Signal spectrum data (606) | Number of matches (608) |
|---|---|---|---|
| | | | |
| | | | |
| | | | |
| | | | |
| | | | |
| | | | |
| | | | |
| | | | |

METHOD AND SYSTEM FOR DYNAMIC LEARNING THROUGH A REGRESSION-BASED LIBRARY GENERATION PROCESS

CROSS-REFERENCE TO RELATED APPLICATIONS

The present application is a divisional application of U.S. patent application Ser. No. 09/923,578 filed Aug. 6, 2001 now U.S. Pat. No. 6,785,638.

TECHNICAL FIELD

The present invention relates to a method and system for efficiently determining grating profiles using dynamic learning in a library generation process.

BACKGROUND ART

Features on semiconductor devices and transmitters of optical fiber links are being formed that are less than one micron in width. Measurement of these sub-micron features is increasingly difficult as the size of the features become smaller. However, knowledge of the dimensions of gratings or periodic structures is essential in order to determine if the dimensions of the features are within the acceptable ranges and if a particular fabrication process causes the sidewalls of the features to be tapered, vertical, T-topped or undercut.

Traditionally, a sample is cleaved and examined with a scanning electron microscope or similar device. This method is slow and expensive. Angular scatterometry has been employed to measure linewidths of gratings, but the process requires a setup of multiple detectors at different angles from the incident beam to measure the diffraction of the scattered light. Again, this is difficult to implement because of the setup required. Another form of angular scatterometry, which only uses zeroth order light, is not very sensitive to sub-100 nm features due to the large wavelength of light typically used by the lasers used in the process.

Spectroscopic reflectometry and ellipsometry are used to direct light on the grating and measure the spectra of reflected signals. Current practices generally use an empirical approach where the spectra of reflected light is measured for a known width of features in a grating. This process is time consuming and expensive even for a limited library of profiles of grating dimensions and the associated spectrum data of reflected light. In another practice, libraries storing large numbers of profiles and signal data need to be built in advance, which requires large upfront processing times and, even then, cover only limited parameter ranges and resolutions. In another practice, real-time regression is used. However, this method covers only a limited parameter range due to the "real-time" nature that limits the amount of time available for simulation and search. In addition, unlike the library approach, a strict real-time regression method does not cover the result space comprehensively, potentially leaving the method mired in local minima, versus properly determining the global minimum.

Thus, there is a need for a less laborious and less expensive method of creating the library of profiles and associated spectrum data. There is also a need for a method and system of creating a dynamic library of grating profiles without first generating a master library, thereby obtaining more rapid searches, exhaustive coverage, and limited or zero upfront processing times.

SUMMARY OF THE INVENTION

The method and system in accordance with embodiments of the present invention relates to a method of determining an actual grating profile. In an aspect of the invention, an embodiment such as a computer receives a set of measurements, including, for example, reflectivity and change in polarization states, to obtain actual spectrum signal data associated with the grating and generates a first trial profile having a first trial spectrum signal data.

In a further aspect of the invention, the computer compares the first trial spectrum signal data to the actual spectrum signal data. If the first trial spectrum signal data does not match the actual spectrum signal data within preset discrepancy criteria, the computer determines a second trial profile better approximating the actual profile by using optimization techniques, such as local and/or global optimization techniques. The computer iteratively generates additional trial profiles in an attempt to find a trial profile having spectrum signal data matching the actual spectrum signal data. When a match of spectrum signal data within preset discrepancy criteria occurs, the computer retrieves the associated matching trial profile.

In another aspect of the invention, an embodiment provides a method and system for setting up a regression optimization. The embodiment receives a set of measurements and selects values for parameters, parameter ranges, and parameter resolutions. The embodiment may run the regression optimization, generate regression results, analyze the generated regression results, and use the generated regression results to adjust parameters, ranges, and/or resolutions.

In another aspect of the invention, an embodiment provides a method and system for determining a profile associated with a grating by receiving a measured signal, selecting a set of trial parameter values, and determining whether the set of trial parameter values is stored in a database. In a further aspect of the invention, if the set of trial parameter values is stored in the database, an embodiment of the invention searches the database for a trial signal associated with the set of trial parameter values.

In another aspect of the invention, an embodiment provides a method for managing a database by selecting or creating a set of parameters, parameter ranges, and parameter resolutions, storing a set of parameter values to the database, and determining whether all value combinations associated with the set of parameters have been stored into the database.

In another aspect of the invention, an embodiment provides a method and system for determining a profile by receiving a set of measurements associated with an actual signal and searching a profile library for a closest matching set of trial parameter values. The set of trial parameter values may be associated with a trial signal. In a further aspect of the invention, the embodiment determines whether the trial signal satisfies a goodness of fit threshold. If the trial signal satisfies the threshold, an embodiment displays the closest matching set of trial parameter values.

BRIEF DESCRIPTION OF THE DRAWINGS

FIG. 6 shows an exemplary table data structure view of a dynamic library associated with the system and/or method in accordance with embodiments of the present invention.

DETAILED DESCRIPTION OF THE PREFERRED EMBODIMENTS

The present invention provides a method and system for efficiently determining grating profiles using dynamic learning in a library generation process. In the following description, numerous details are set forth in order to enable a thorough understanding of the present invention. However, it will be understood by those of ordinary skill in the art that these specific details are not required in order to practice the invention. Further, well-known elements, devices, process steps and the like are not set forth in detail in order to avoid obscuring the present invention.

Although the invention has been described in conjunction with particular embodiments, it will be appreciated that various modifications and alterations may be made by those skilled in the art without departing from the spirit and scope of the invention. The invention is not to be limited by the foregoing illustrative details, but rather is to be defined by the appended claims.

Figure 1:
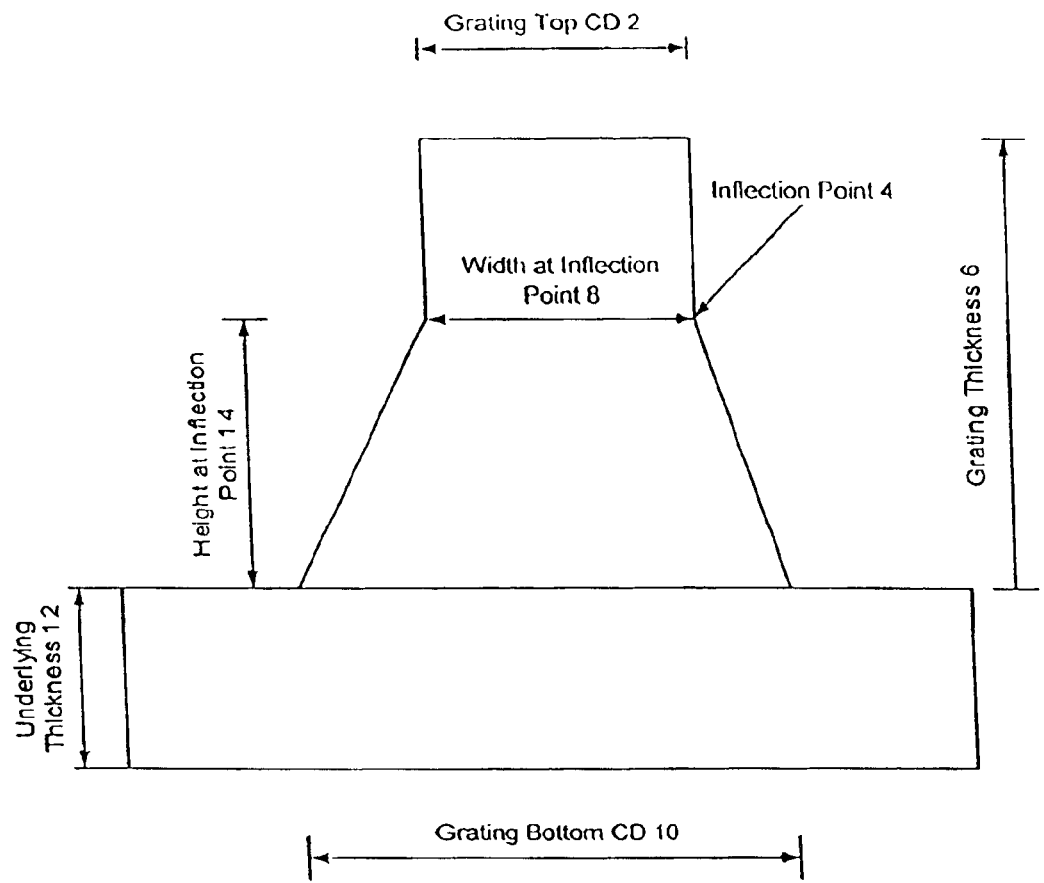
FIG. 1 shows an exemplary architectural diagram illustrating a grating feature associated with the system and/or method in accordance with embodiments of the present invention.

FIG. 1 shows an exemplary architectural diagram illustrating a grating feature associated with the system and/or method in accordance with embodiments of the present invention. FIG. 1 is an architectural diagram illustrating the critical dimensions (CD) of a grating feature in one embodiment of the present invention. The cross-sectional view of a feature in a grating has a grating top CD 2, grating bottom CD 10, a grating thickness 6, and underlying thickness 12. Other dimensions are the width at inflection point 8 and the height at the inflection point 14. The inflection point 4 is the point in the sidewall of the feature where the slope changes. The percent height at inflection point is defined as the ratio of the height at inflection 14 to the grating thickness 6. Some applications may include other feature measurements such as the magnitude of T-topping, footing, rounding, undercut, concave sidewalls, and convex sidewalls as well as the angle of intersection of the sidewall and the underlying thickness.

Figure 2:
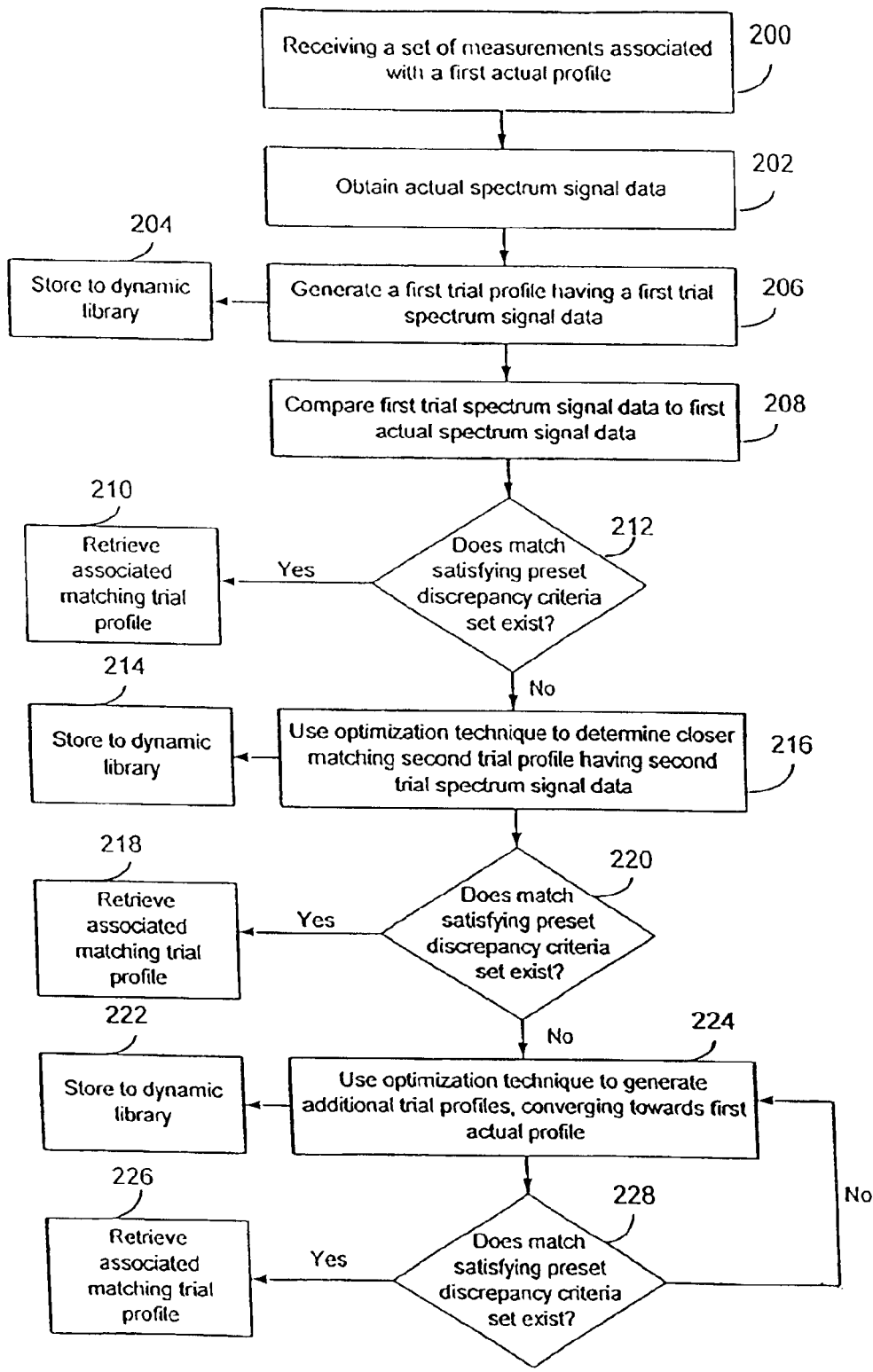
FIG. 2 shows a flowchart overview of an exemplary dynamic library generation and matching process associated with the system and/or method in accordance with embodiments of the present invention.

FIG. 2 shows a flowchart overview of an exemplary dynamic library generation and matching process associated with the system and/or method in accordance with embodiments of the present invention. At step 200, an embodiment of the present invention, collects a set of measurement data associated with a first actual profile for a grating.

In an embodiment of the invention, diffraction data may be acquired from one-dimensionally and two dimensionally repeating, regularly spaced series of structures using optical metrology. For example, the previously referenced patent application "Generation of a Library of Periodic Diffraction Signals" describes the acquisition of such diffraction data and is hereby incorporated by reference in its entirety.

Based on the set of collected measurements, a system associated with an embodiment of the present invention, such as a computer, generates actual spectrum signal data 202. The method of generating spectrum signal data by the computer is generally well-known by one of ordinary skill in the art. For example, spectrum data can refer to the data representing the digitized measurements of the reflected light from a grating. On the other hand, calculated spectrum data may be derived for a hypothetical grating by solving a rigorous mathematical model with a given set of parameter dimensions. One such mathematical model is described in "An Integrated System of Optical Metrology for Deep Sub-Micron Lithography", University of California at Berkeley Doctoral Thesis of Xinhui Niu, Apr. 20, 1999, which is incorporated here by reference in its entirety. The previously referenced patent application, "Caching of Intra-Layer Calculations for Rapid Rigorous Coupled-Wave Analyses," also describes derivation of the spectrum data.

In an embodiment, actual spectrum data may be obtained by using an optical metrology device. Examples of optical metrology devices include spectroscopic ellipsometers, spectroscopic reflectometers, and variable angle, single wavelength reflectometers and ellipsometers.

Referring again to FIG. 2, at step 206, an embodiment of the present invention selects a first set of trial parameters associated with a first trial profile. In an embodiment, the values for the first set of trial parameters may be, for example, selected randomly from within a specified range of values for the parameters. For instance, the range for a parameter may be based on a spread around an expected value for that parameter. Tile computer may generate a first set of trial spectrum signal data from the first set of trial parameters.

In an embodiment, the computer stores the first trial profile and the first set of trial spectrum signal data to a dynamic library of profiles and spectrum data. In step 204, the dynamic library may be stored on, for example, a database on a hard drive or other storage device associated with an embodiment of the invention.

At step 208, the computer compares the first set of trial spectrum signal data to the first set of actual spectrum signal data. The comparison may be a matching test performed to determine whether preset criteria is satisfied in step 212. One exemplary matching test that is well known in the art is a Minimum Least Squares Error (MLSE) algorithm, wherein each measured variable in the first trial spectrum signal data is subtracted from respective variable in the first actual spectrum signal data. This difference is then squared to obtain an error estimate. The squared differences may then be summed over all of the measured variables to obtain an estimate of the total error of the first trial spectrum signal data. If the total error is less than the preset maximum permitted error, then the computer considers that there is a match and retrieves the matching trial profile associated with the matching first trial spectrum signal data 210.

For instance, the following equation may be used by the least cost algorithm:

$$Cost = \sum_{i=i}^{n}(y_i - \hat{y}_i)^2$$

where $y_i$ is the trial data for element i; and $\hat{y}_i$ is the actual data for element i Referring again to step 212, if the total error surpasses the preset maximum permitted error, then the first trial spectrum signal data is considered not to match the first actual spectrum signal data. The computer uses an optimization technique to determine a second trial profile having an associated second trial set of spectrum signal data 216. Exemplary optimization techniques that may be used by the computer include global optimization techniques such as simulated annealing and local optimization techniques such as a steepest descent algorithm.

Optimization methods for intelligently selecting increasingly better trial sets of values, such as those having greater goodness of fit, include but are not limited to steepest descent methods. In an exemplary simplified steepest descent algorithm, a first guess or trial set of values may be randomly selected, and an error metric is generated when compared to the measured signal. A second trial set may also be randomly generated. If the error metric for the second trial set when compared to the measured signal is better, for example goodness of fit is greater or better, then, the third trial set of values is selected in the direction of the second trial set. If the error metric for the second trial set is worse, then the values for the third trial set are varied in the opposite direction. For example, if multiple dimensions for the regression model are needed, for example four dimensions for a set of four measured parameters, then a larger set of random trial sets of values may be needed before intelligent variation of values using a steepest descent algorithm can be made.

The second trial profile and second trial set of spectrum signal data may be stored to the dynamic library of profiles and spectrum data 214. In an embodiment, the library is dynamic and grows as trial measurement records are generated and stored to the library and may occur as actual measurements are taken.

The computer determines whether the second trial set of spectrum signal data matches the first actual spectrum signal data 220. The match test may be based on preset discrepancy criteria, such as by using an MLSE test. If the second trial set of spectrum signal data satisfies the preset criteria, the second trial set of spectrum signal data matches, and the computer retrieves the matching trial profile associated with the matching second trial set of spectrum signal data 218.

If the second trial set of spectrum signal data does not match the first actual spectrum signal data, the profiles do not match, and the computer uses an optimization technique to iteratively generate additional trial profiles 224. For example, a steepest descent algorithm may be used to interatively generate additional trial profiles.

In step 224, each additional trial profile is associated with an additional trial set of spectrum signal data. Each additional set of spectrum signal data is tested to determine if it matches the first actual spectrum signal data 228. During the iterative process, each additional trial profile and associated additional trial set of spectrum signal data may be stored to the dynamic library of profiles and spectrum data 222.

When the computer finds a match of spectrum signal data in step 228, the computer retrieves the associated matching trial profile 226.

Figure 3:
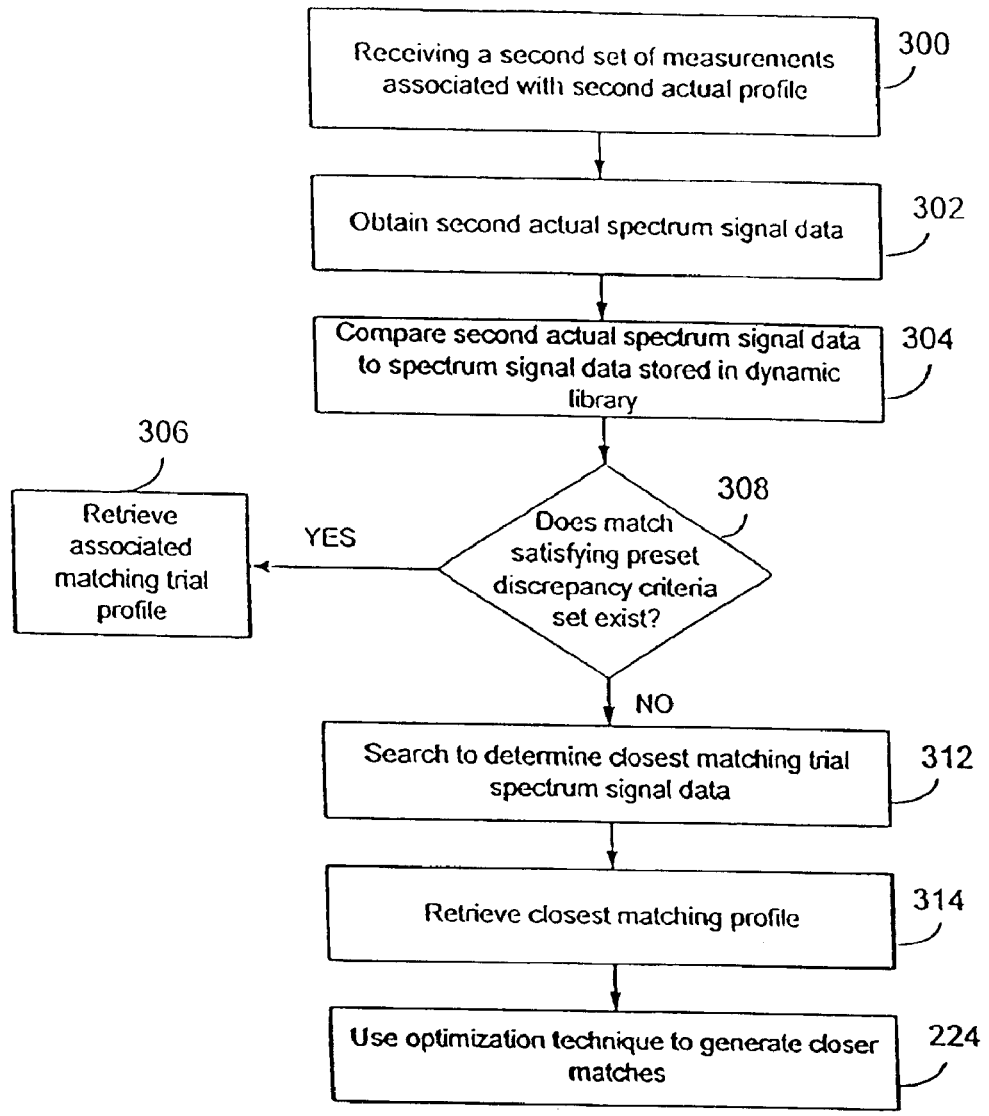
FIG. 3 shows a flowchart overview of an exemplary dynamic library search and matching process associated

FIG. 3 shows a flowchart overview of an exemplary dynamic library search and matching process associated with the system and/or method in accordance with embodiments of the present invention. As a computer associated with an embodiment of the invention determines matches for one or more actual profiles, the computer systematically builds the dynamic library of profiles and spectrum data, which contains sets of trial profiles and associated trial spectrum signal data. At step 300, the computer receives a second set of measurements associated with a second actual profile. From these measurements, the computer obtains a set of second actual spectrum signal data 302.

In step 304, the computer searches the trial spectrum signal data stored in the dynamic library of profiles and spectrum data. The computer may use, for example, an MLSE algorithm to determine whether a match of spectrum signal data satisfying preset discrepancy criteria exists 308, as previously described.

In an embodiment of the invention, if the trial set of spectrum signal data having the lowest least squared error value when compared to the second actual spectrum signal data has a lower error value than the maximum preset error limit, then the computer deems the trial set of spectrum signal data to be a match and retrieves the associated matching trial profile 306.

If the lowest error value surpasses the maximum preset error limit, then no match is deemed to exist, and the computer searches the dynamic library to determine the closest matching trial spectrum signal data 312. In an embodiment of the invention, the computer may assume the trial set of spectrum signal data having the lowest least cost error value as found in step 308 to be the closest match and retrieve the associated closest matching profile 314. The computer may use an optimization technique to iteratively generate closer matching profiles in step 224, during which the computer analogously follows the exemplary process shown in step 224 of FIG. 2.

Figure 4:
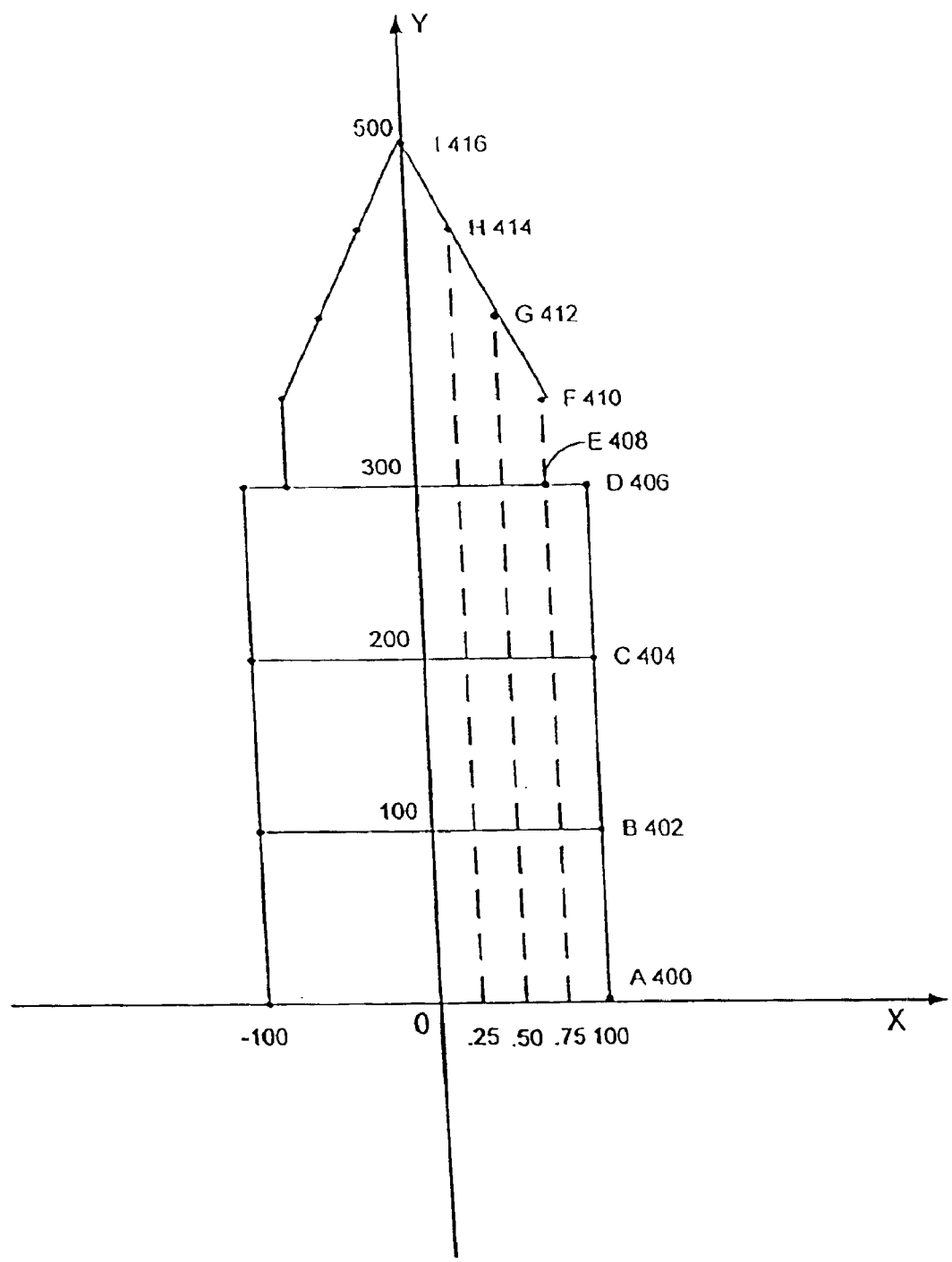
FIG. 4 shows an exemplary architectural shape-profile element view of a grating in accordance with embodiments of the present invention.

FIG. 4 shows an exemplary architectural shape-profile element view of a grating in accordance with embodiments of the present invention. The exemplary grating profile shown in FIG. 4 is symmetrical about the Y-axis. In such a symmetrical profile, points A 400, B 402, C 404, D 406, E 408, F 410, G412, H 414, and I 416 associated with the shape of half of the profile may be used to determine the shape of the entire profile. For example, point A 400 is associated with location (100, 0), which is located along the X-axis. The scale of the profile may be in nanometers or another scale. Similarly, point B 402 is associated with location (100, 100). Point C 404 is associated with location (100, 200). Point D 406 is associated with location (100, 300). Point E 408 is associated with location (75, 300). Point F 410 is associated with location (75, 350). Point G 412 is associated with location (50, 400). Point H 414 is associated with location (25, 450). Point I 416 is associated with location (0, 500), which is located along the Y-axis.

FIG. 6 shows an exemplary table data structure view of a dynamic library associated with the system and/or method in accordance with embodiments of the present invention. Dynamic library table 600 can includes fields such as entry ID 602, shape-profile data 604, signal spectrum data 606, and number of matches 608. In an embodiment of the invention, each row of the table contains data associated with a trial grating profile.

Entry ID 602 may be a identifier associated with a record for the trial grating profile. Shape-profile data 604 may include coordinates for points associated with the shape of the trial grating profile, such as points A 400, B 402, C 404, D 406, E 408, F 410, G412, H 414, and I 416 referenced above and shown in FIG. 4.

$$Cost = \sum_{i=i}^{n}(y_i - \hat{y}_i)^2$$

where $\hat{y}_i$ is tan($\psi$) cos($\Delta$)

Figure 7:
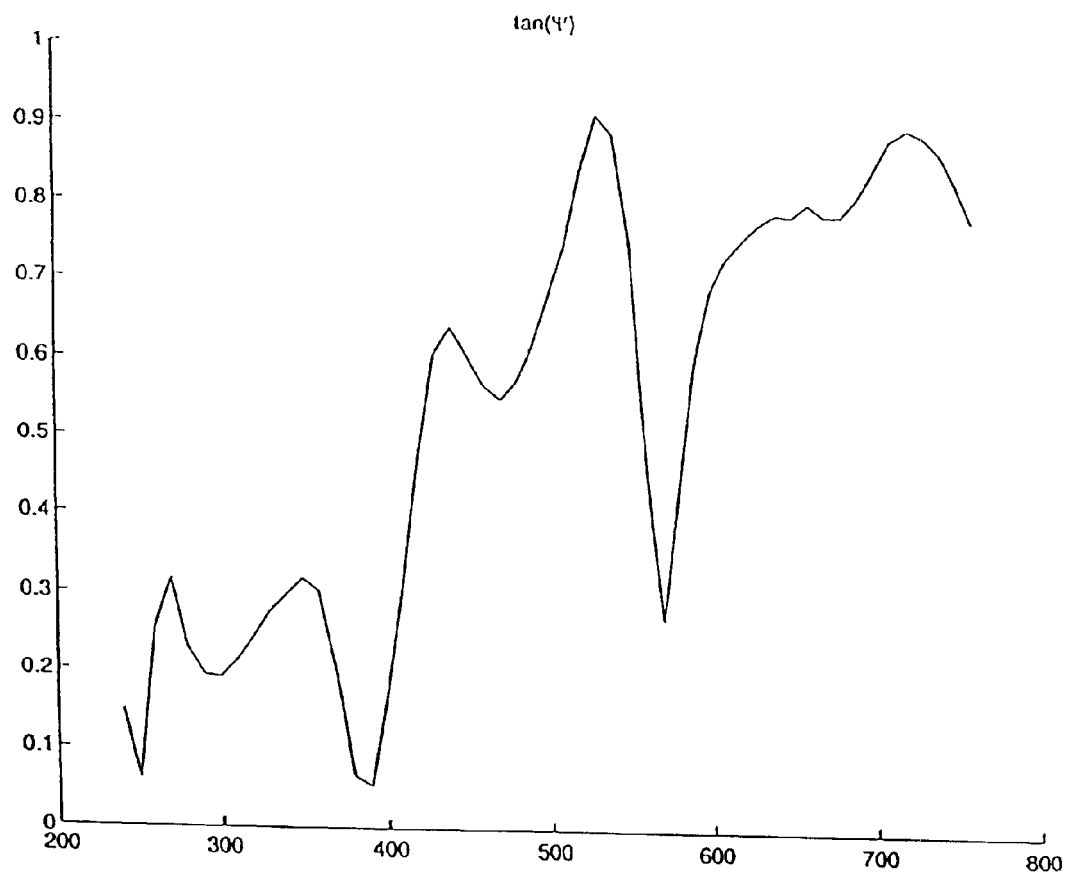
FIGS. 7 and 8 show exemplary diagrams associated with signal spectrum data for a trial grating profile in an embodiment of the invention.
Figure 8:
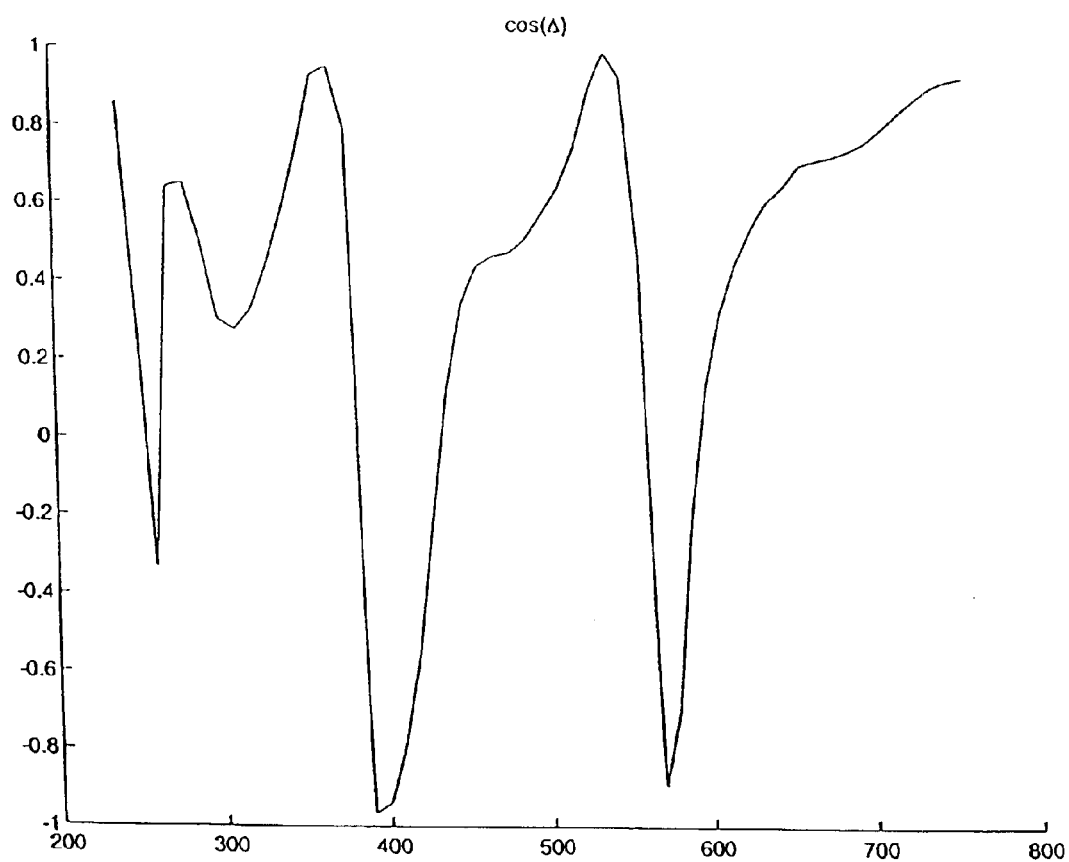
Figure 9:
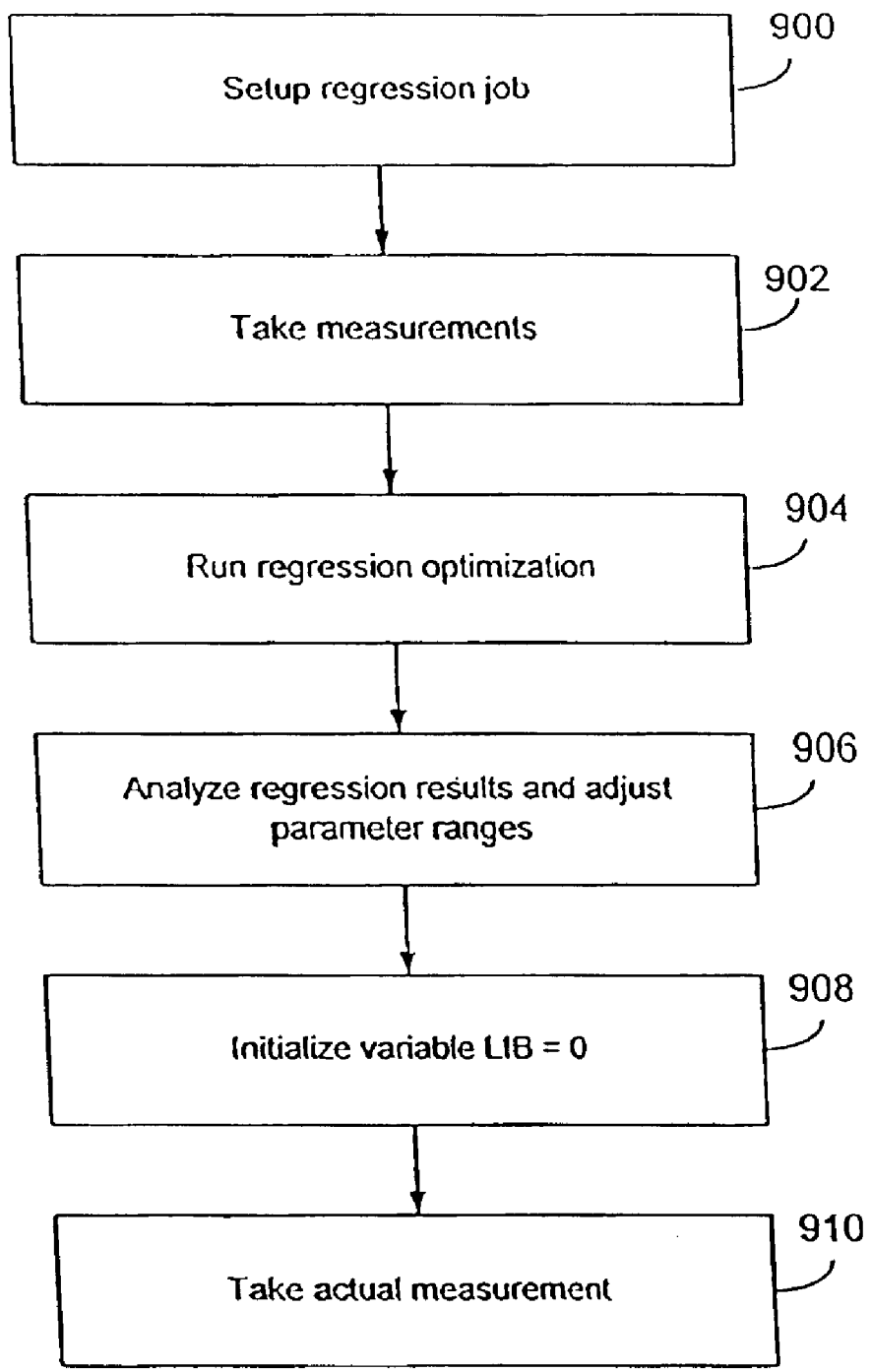
FIGS. 9–12 show a flowchart representation of another embodiment of the method and system of the present invention.

Signal spectrum data 606 includes spectrum data associated with the trial grating profile. FIGS. 7 and 8 show exemplary diagrams associated with signal spectrum data for a trial grating profile in an embodiment of the invention FIG. 7 shows signal spectrum data for a tan ($\psi$) measurement associated with an exemplary grating in accordance with embodiments of the invention. FIG. 8 shows signal spectrum data for a cos ($\Delta$) measurement associated with an exemplary grating.

Referring again to FIG. 6, number of matches 608 can include a counter showing the number of times the trial grating profile matches an actual grating profile by satisfying preset discrepancy criteria. For example, the counter for each trial grating profile may be initialized to 0. Each time a trial grating profile matches an actual grating profile, the counter for that trial grating profile is increased by 1.

In an embodiment of the invention, total dynamic library size may be managed by having a maximum number of stored trial grating profile records. If the maximum number is surpassed, in an exemplary embodiment, records for the least-used trial grating profiles may be deleted. For example, the record for the trial grating profile having the lowest value in the number of matches 608 field may be deleted. Ties may be broken, for example, by a first-in-first-out tiebreaker, wherein the earliest created trial grating profile is deleted.

In another embodiment of the invention, the entire dynamic library may be managed by a first-in-first-out system. In this embodiment, number of matches 608 is not used to determine trial grating profile deletion.

FIGS. 9–12 show a flowchart representation of another embodiment of the method and system of the present invention. A computer associated with the an embodiment of the method and system of the present invention sets up a regression model 900 to prepare for the analysis of grating profiles. The regression model is setup 900 in order to find the best set of values for various parameters that can be used to parameterize a grating profile. At setup step 900, the software associated with the computer sets up parameterizations, ranges, and resolutions within each range for each parameter.

For instance, an exemplary embodiment of the software may be configured for a polysilicon on oxide on silicon structure. The polysilicon may be patterned, whereas the oxide and silicon may be unpatterned. The polysilicon layer may, for example, have a bottom critical dimension (CD), a sidewall angle, and a thickness parameter. The oxide may have a thickness parameter. For the bottom CD parameter, the software may setup the range to be between 100 nanometers to 120 nanometers. The range for the sidewall angle may be, for example, 82 degrees to 88 degrees. An exemplary range for the polysilicon thickness may be from 200 to 220 nanometers. An exemplary range for the oxide thickness may be from 1.0 to 1.2 nanometers. For each parameter range, a resolution may be arbitrarily set, for example 1 nanometer.

At step 902, the computer takes the standard measurements for a signal associated with patterned areas of grating profiles. Regression analysis is then run 904.

For example, a first set of values for the parameters within the specified ranges may be selected. A simulation may then be run on the first set of values. The simulation is compared to the measured signal, and the differences between the first set of values and the measured signal are stored or analyzed, for example as an error metric. A second set of values for the parameters may be selected. A simulation is run on the second set, and the results are compared to the measured signal, and a second error metric is generated. The regression is run until a goodness of fit value, for example 0.9, is met or exceeded. At that point, the set of values generating the signal best approximating the measured signal is deemed to be the correct set of parameter values for the measured signal.

As previously described, optimization methods for intelligently selecting increasingly better trial sets of values (those having greater goodness of fit) include but are not limited to steepest descent methods.

Step 904 may be run on, for example, a 16-processor machine for 5 measurement signals during initialization. In an exemplary embodiment, the computer then analyzes the regression results for the 5 results, adjusting parameterizations, ranges, and resolutions 906. Step 906 may be used to narrow or widen the range of expected values for each parameter based on the 5 results.

For instance, if the initially selected range for a parameter is 100 nanometers to 200 nanometers, but all of the results from the 5 measurements fall between 110 nanometers and 120 nanometers, the new range for the parameter when performing the real-time regression analysis may be modified to be closer to the 110–120 nanometer range. In an embodiment, step 906 may be performed off-line, or by a different set of processors.

At step 908, the software may initialize a variable LIB to 0. The value of 0 may indicate, for example, that a library of profiles and signals has not yet been created or completed.

Figure 10:
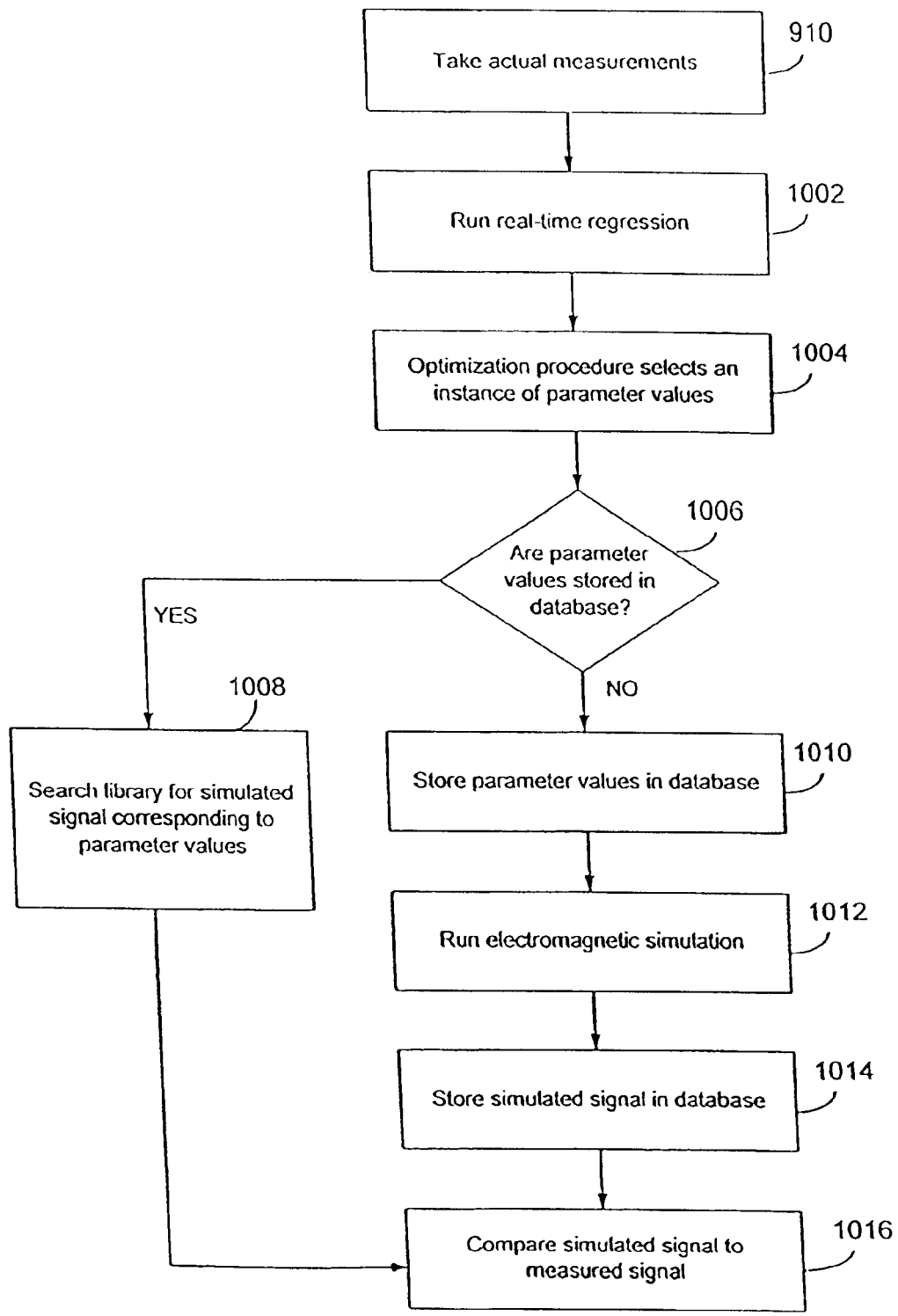

While LIB=0, one or more actual measurements from a grating profile may be taken 910. Referring to FIG. 10, real-time regression 1002 may be run for the actual measurements on a 16-processor computer using the determined parameterization (set of parameters), ranges, and resolutions. The regression seeks to find the best set of values for the parameters to obtain a satisfactory fit with the measured signals. For example, an optimization procedure associated with the real-time regression may select an instance of parameter values 1004. The computer checks to determine if the parameter values for the selected instance are stored in a database associated with the computer 1006. While the regression is being performed, a library is built in parallel. During the regression process, trial sets of values are selected 1004. These intermediate trial sets of values and their associated simulated signals are useful and may be stored in the library. If the values are not already stored, the computer stores the values in the database 1010. An electromagnetic simulation is run on the selected instance of parameter values 1012, and the simulated signal or signals are stored in the database 1014.

The computer can then compare the simulated signal to the measured signal 1016. Referring to step 1006, if the parameter values had already been stored in the database, then the computer searches the library for the simulated signal corresponding to the parameter values 1008. Upon retrieving the simulated signal, it is compared to the measured signal 1016.

Figure 11:
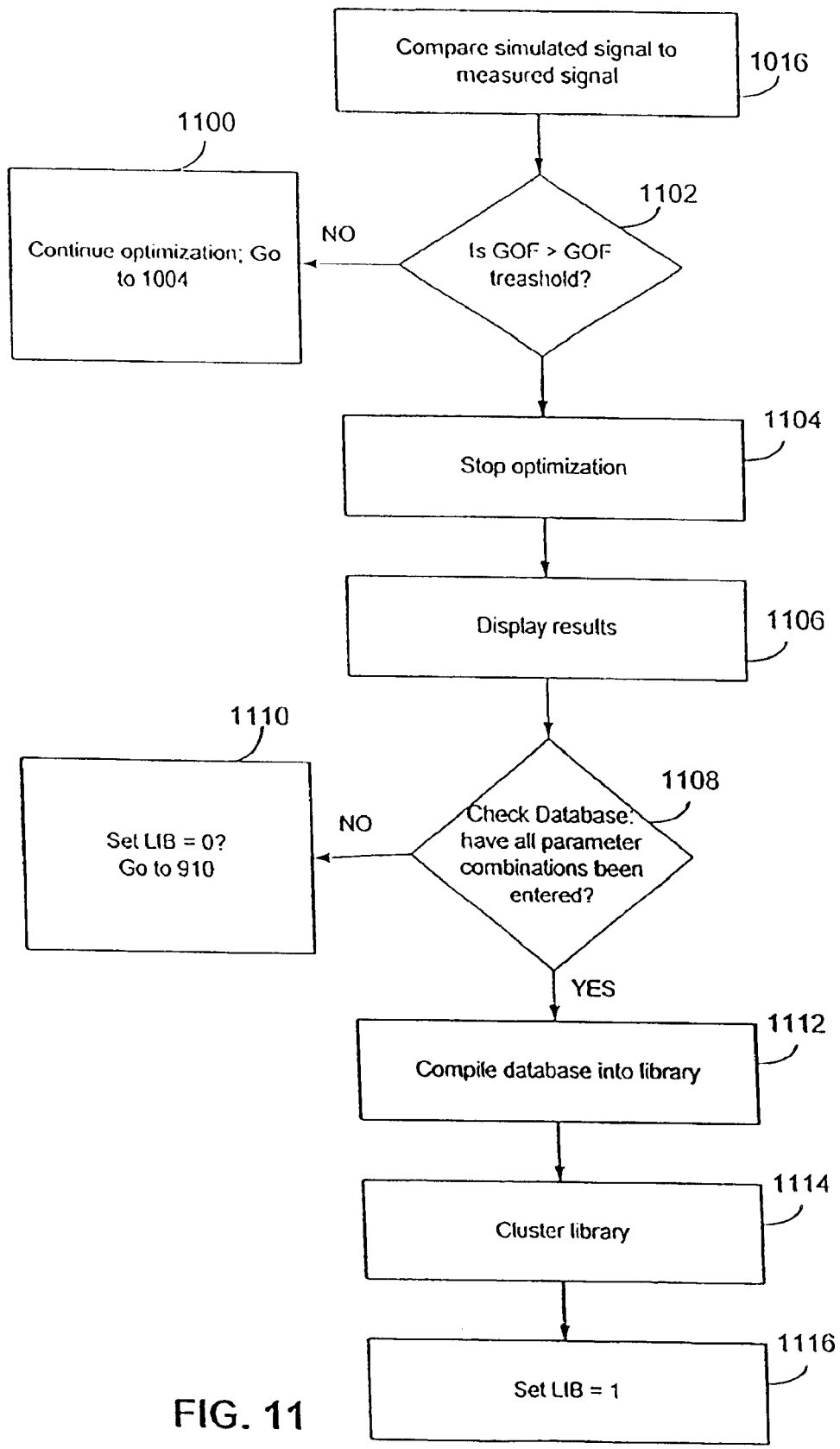

Referring to FIG. 11, when comparing the simulated signal to the measured signal 1016, the computer determines whether the goodness of fit threshold is met 1102. For example, if the goodness of fit threshold is set to be 0.9, if the goodness of fit between the simulated and measured signals is below 0.9, then the optimization continues 1100 by proceeding to step 1004 in FIG. 10 and selecting another instance of parameter values. Referring again to FIG. 11, if the goodness of fit threshold is met, then the optimization is stopped 1104, and the results of the optimization may be displayed 1106.

At step 1108, the computer checks the database to determine if all parameter combinations have been entered. For instance, for a simplified parameter set of three, for example a bottom CD, a height, and a width. For the bottom CD if the range is 100 to 120 nanometers, and the resolution is 1 nanometer, then there are 21 possible parameter values for bottom CD. If there are also 21 possible values for height and 21 possible values for width, there are a total of 21×21×21=9261 possible parameter value combinations. The computer checks to see if all 9261 combinations have been simulated and stored in the database. If not all 9261 combinations have been simulated and stored, then at step 1110, the computer returns to step 910 in FIG. 10 to take the next measurement and continue building the database.

Referring again to FIG. 11, if all of the parameter combinations have been entered, then the database is complete for the specified parameterizations, ranges, and resolutions. The computer then compiles the database into a library 1112. As an example, the database and library may be stored in a hard drive of a computer but may be stored in any other associated location and/or storage device. The computer may also optionally cluster the library 1114, as described in the patent application entitled "Clustering for Data Compression," Ser. No. 09/727,531, filed Jul. 28, 2000, which is incorporated by reference in its entirety. At step 1114, the computer may compress the library to allow for more efficient searching. The library variable LIB is then set to 1 at step 1116 to indicate that the library has been completed.

Figure 12:
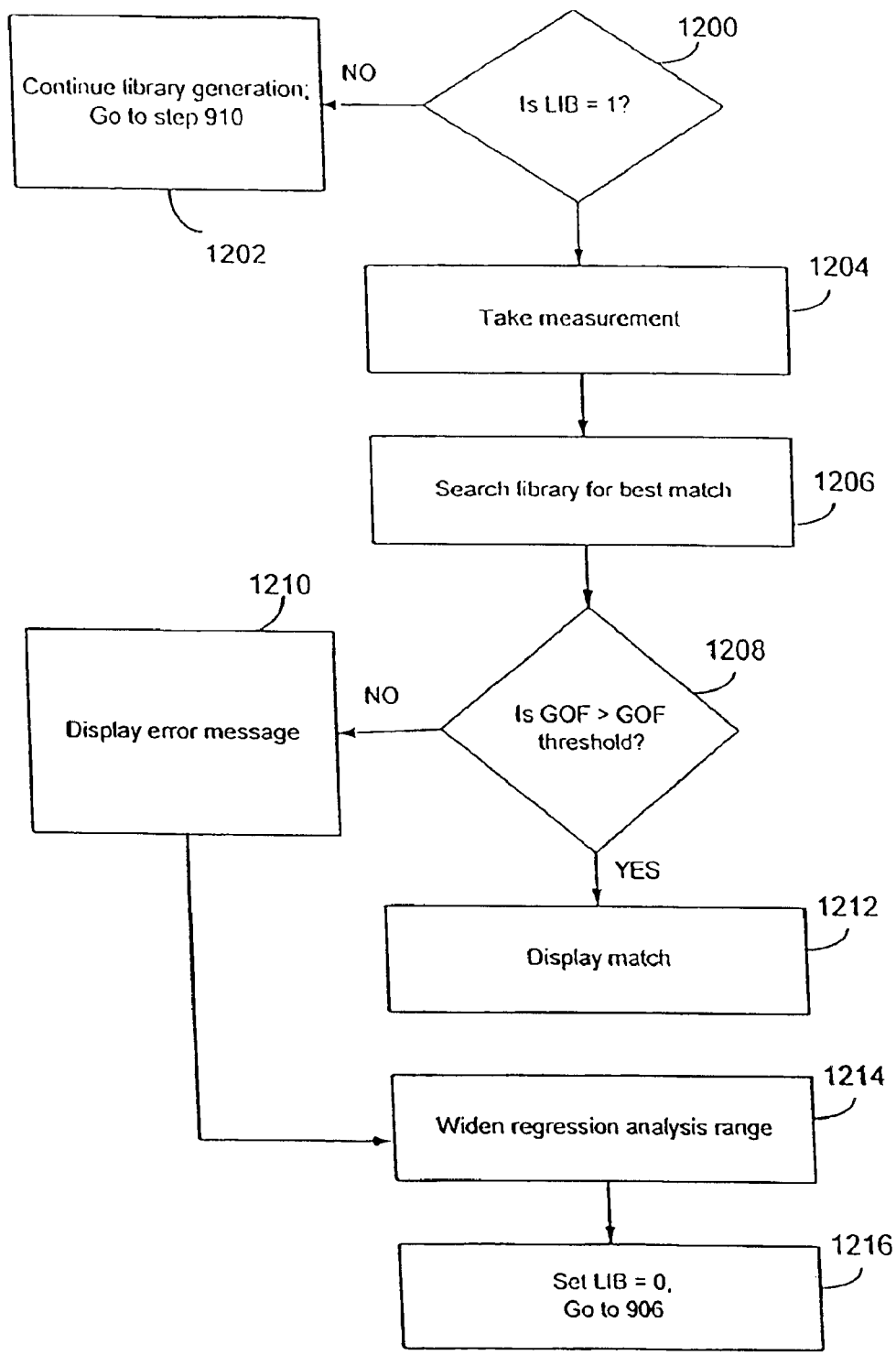

Continuing to FIG. 12, the computer checks to determine if LIB=1 at step 1200. If LIB is not=1, then the computer continues the library generation process in parallel 1202 and returns to step 910 in FIG. 10 to take the next measurement. Referring again to FIG. 12, if LIB=1, then the computer takes the next measurement 1204. The computer can search the library for the best match 1206. If the best match satisfies the goodness of fit threshold in step 1208, then the match may be displayed 1212. If the best match does not satisfy the goodness of fit threshold, then the computer can display an error message 1210 indicating that the library does not contain a matching entry. The computer may also flag that the gratings generated have drifted outside of the preferred range and may recommend that a manufacturing process be paused or stopped pending further review.

In an embodiment, the computer may then determine how much to widen the regression analysis range for the parameters in step 1214. The amount by which the ranges are widened may be specified in terms of percentages by a user of an embodiment of the invention. For example, the user may specify that if the Goodness of Fit (GOF) is below the GOF threshold, the ranges for all parameters should be increased by 30%. For example, the computer may determine whether the values are slightly outside the specified ranges or whether they have departed greatly from the ranges by determining how poor the GOF value is. In an embodiment of the invention, the computer then sets the library variable LIB to 0 in step 1216 and progresses to step 906 in FIG. 9 to adjust the parameter ranges, widening them if necessary, before taking the next measurement 910. In an embodiment of the invention, while LIB=0, the computer can continuously generate the library database, even if no actual regression analysis is being performed.

Figure 13:
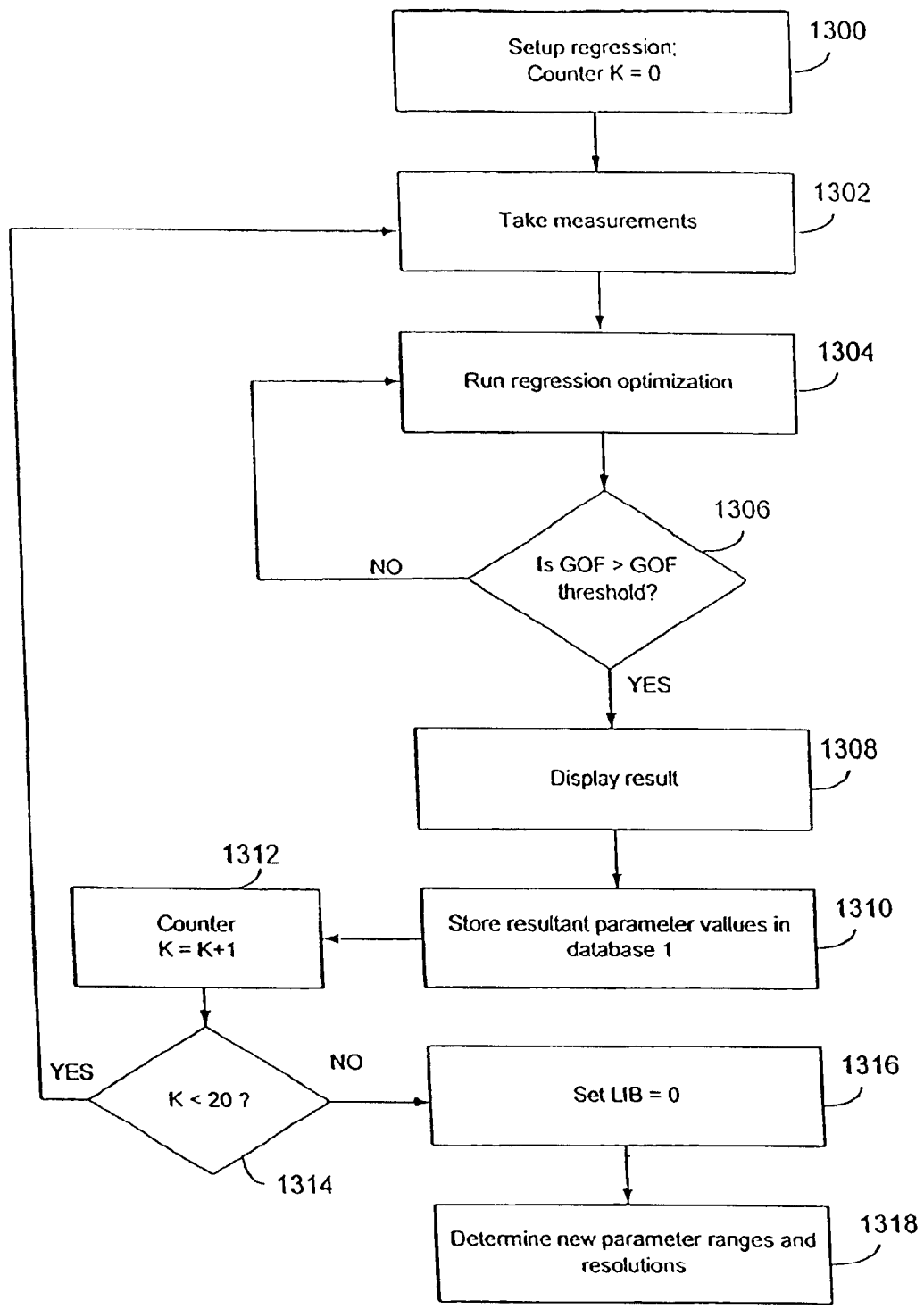
FIGS. 13–14 show a flowchart representation of another embodiment of the method and system of the present invention.
Figure 14:
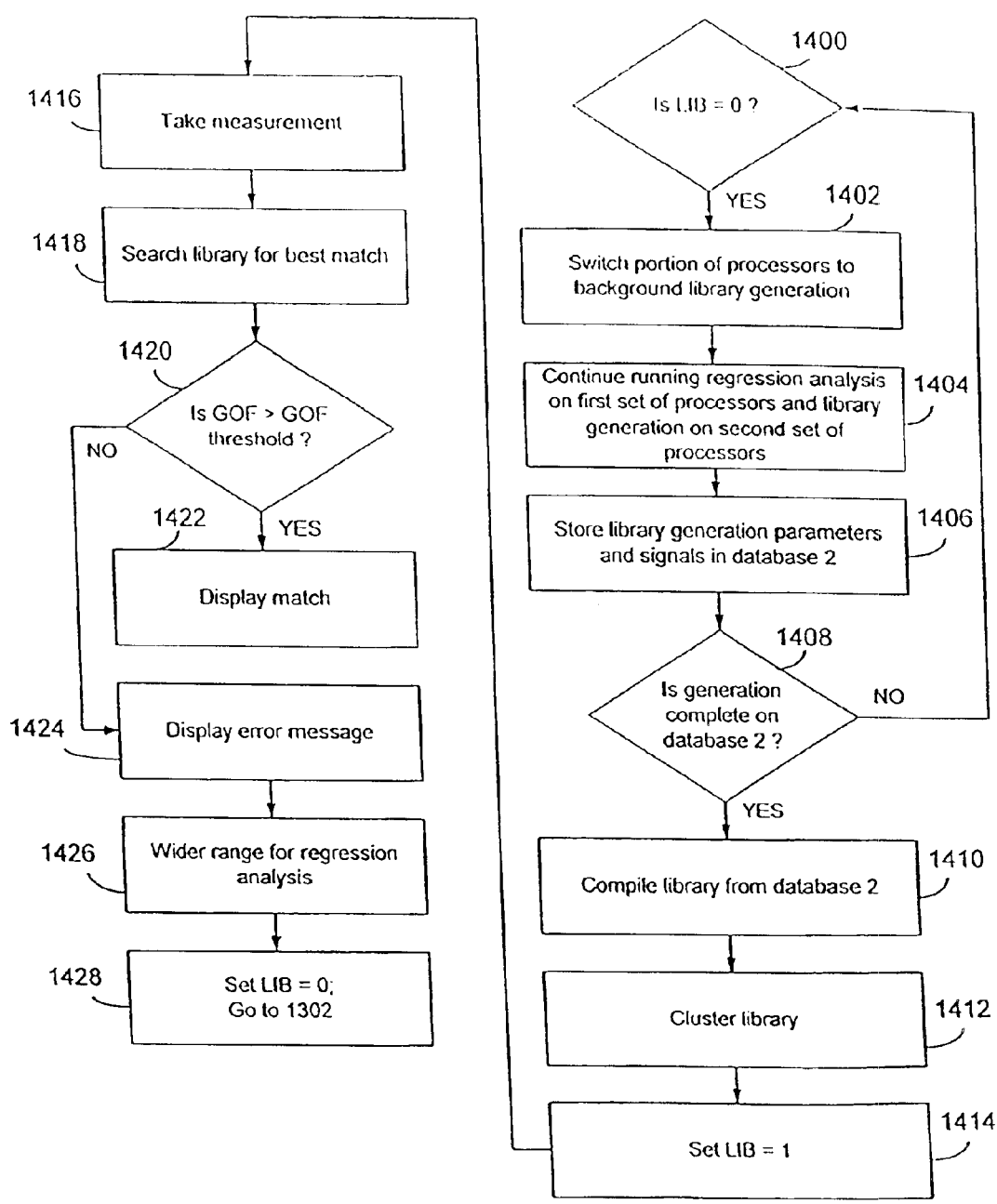

FIGS. 13–14 show a flowchart representation of another embodiment of the method and system of the present invention. In this embodiment, not all trial values and associated simulated signals are stored. For example, only the trial values and simulated signals that match, subject to a goodness of fit threshold, the measured signals, may be stored.

Referring to FIG. 13, at step 1300, the computer perform regression setup, specifying parameterizations and their associated ranges and resolutions and initializing a measurement counter K to 0. In an exemplary embodiment, the regression may be set up on a 15-processor machine or computer. Measurements for a grating profile may then be taken at step 1302. The computer may run a regression optimization 1304 until a goodness of fit threshold is reached 1306. When the goodness of fit threshold is met, the computer may display the results 1308 and store the resultant parameter values and simulated signals in first database 1310.

In an exemplary embodiment, the computer may run the regression analysis for 20 measurements 1314. A greater or fewer number of measurements may also be employed by an embodiment of the invention. After the $20^{th}$ measurement, the computer sets library variable LIB to 0 at step 1316 and determines the new parameter ranges and resolutions 1318 based on the parameter values for the 20 measured signals. For example, for each parameter, the lower end of the range for the parameter may be set at the lowest value among the 20 measurements, and the higher end may be set at the highest value among the 20 measurements. In another embodiment, the lower end of the range may be set at 20% below the lowest measured value, and the higher end may be set at 20% above the highest measured value. Other cushion values may also be used.

Referring to FIG. 14, while LIB=0, the computer may switch a portion of the associated processors to continue performing background library generation 1402 to obtain spectra and signals for all combinations of parameter values within the specified parameter ranges. In an embodiment of the invention, regression analysis may be run on a first set of 8 processors while library generation is run on a second set of 8 processors 1404. Library generation parameters and signals may be stored in a second database 1406. The computer may check to determine if library database generation has been completed on the second database 1408, for example by analyzing whether all combinations of parameter values within the specified parameter ranges have been simulated and stored. If the database has not been completed at step 1410, an embodiment of the method returns to step 1400 to continue library database generation and regression analysis. Once generation of the second database has been completed in step 1408, the library is compiled from database 2 at step 1410. Optionally, the computer may cluster the library at step 1412 and set library variable LIB=1 at step 1414.

If LIB=1, then, the next measurement may be taken 1416, and the computer searches the library for the best matching signal 1418. Upon retrieving the associated best matching parameter value set, the computer checks the goodness of fit for the parameter values. If the goodness of fit threshold is met 1420, then the match may be displayed 1422. If the goodness of fit threshold is not met, an error message may be displayed 1424. The range of parameter values may also be analyzed and widened for regression analysis at step 1426, and the library variable LIB may be set to 0 at step 1428. An embodiment of the method and system of the present invention may then return to step 1302 to take an additional set of measurements and determine new ranges and/or parameterizations.

Figure 5:
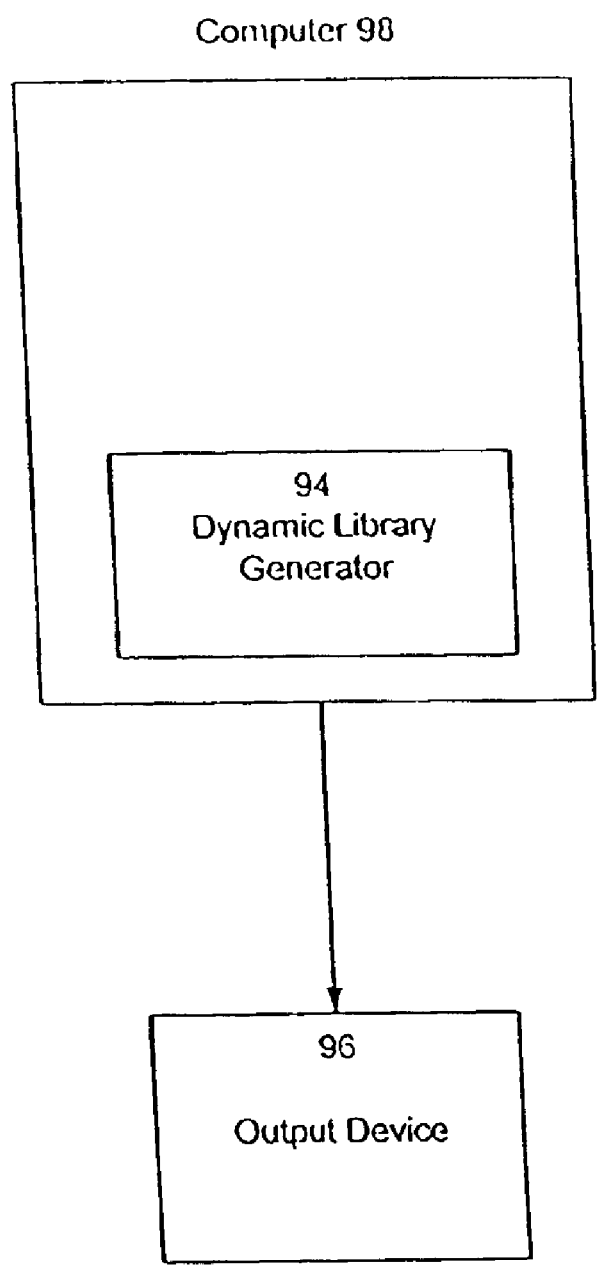
FIG. 5 shows an exemplary architectural diagram illustrating a grating profile dynamic library generator associated with the system and/or method in accordance with embodiments of the present invention.

FIG. 5 shows an exemplary architectural diagram illustrating a grating profile dynamic library generator associated with the system and/or method in accordance with embodiments of the present invention. Library generator 94 may be, for example, a software program associated with or operable in computer 98. The library generator 94 creates a library, such as the library generated at step 204 of FIG. 2, and stores the library in output device 96. In an embodiment of the invention, output device 96 can be a hard drive, a compact disk, a tape drive, or another storage medium associated with computer 98. In another embodiment, the output device 96 may also be located in a location remote from computer 98 and accessible over a network such as the Internet. Computer 98 may be, for example, one computer or a server farm.

Although the invention has been described in conjunction with particular embodiments, it will be appreciated that various modifications and alterations may be made by those skilled in the art without departing from the spirit and scope of the invention. The invention is not to be limited by the foregoing illustrative details, but rather is to be defined by the appended claims.

What is claimed is:

1. A method of setting up a regression optimization, comprising:

receiving a measured signal;

selecting values for one or more members selected from the group consisting of at least one parameter, at least one range associated with the at least one parameter, and at least one resolution associated with the at least one range;

running the regression optimization using the selected values, wherein one or more simulations are run during the regression optimization, and wherein the one or more simulations are compared to the measured signal during the regression optimization;

generating regression results associated with the running of the regression optimization;

analyzing the generated regression results; and using the generated regression results to adjust at least one member selected from the group consisting of the at least one parameter, the at least one range, and the at least one resolution.

2. The method of claim 1, wherein the measured signal is measured from a grating profile.

3. The method of claim 1, wherein the at least one parameter includes at least one member selected from a top cd, a bottom cd, a sidewall angle, and a thickness.

4. The method of claim 1, wherein running the regression optimization comprises:

a) running a simulation for a set of values for one or more selected parameters within one or more selected ranges;

b) comparing the simulation with the measured signal; and c) if the comparison in b) does not meet a goodness of fit, iterating a) and b) using another set of values.

5. The method of claim 4, further comprising:

d) before a), determining if the set of values exists in a database;

e) if the set of values does not exist in the database, performing a), b), and c), then storing the set of values and a simulated signal generated during the simulation in the database; and f) if the set values exists in the database, i) retrieving a simulated signal corresponding to the set of values from the database;

ii) comparing the simulated signal with the measured signal; and iii) if the comparison in ii) does not meet the goodness of fit, iterating d), e), and f) using another set of values.

6. The method of claim 5, further comprising:

determining if all value combinations associated with the set of values have been aimed in the database;

if all of the value combinations have not been stored in the database, continuing to perform a) through f); and if all of the value combinations have been stored in the database, compiling the database into a library.

7. The method of claim 6, wherein determining if all value combinations comprises:

for a selected parameter, a selected range associated with the parameter, and a selected resolution associated with the selected range, determining if all values for the selected parameter within the selected range at the selected resolution have been stored in the database.

8. A method of setting up a regression optimization, comprising:

determining a first set of regression parameters;

receiving a first set of measurements associated with a first profile;

running the regression optimization on the first set of measurements to obtain a first set of resultant parameter values associated with the first profile;

storing the first set of resultant parameter values to a storage location;

receiving a second set of measurements associated with a second profile;

running the regression optimization on the second sat of measurements to obtain a second set of resultant parameter values associated with the second profile; and determining a second set of regression parameters, wherein the second set of regression parameters is associated with at least one member selected from the group consisting of the first set of resultant parameter values and the second set of resultant parameter values.

9. A method of setting up a regression optimization, comprising:

determining a first set of one or more regression parameter ranges;

receiving a first set of measurements associated with a first profile;

running the regression optimization on the first set of measurements to obtain a first set of resultant parameter values associated with the first profile;

storing the first set of resultant parameter values to a storage location;

receiving a second set of measurements associated with a second profile;

running the regression optimization on the second set of measurements to obtain a second set of resultant parameter values associated with the second profile; and determining a second set of one or more regression parameter ranges, wherein the second set one or more regression parameter ranges is associated with at least one member selected from the group consisting of the first set of resultant parameter values and the second set of resultant parameter values.

10. A computer program product for use in setting up a regression optimization, said computer program product comprising:
   a computer usable medium including computer readable program code embodied in said medium for causing setting up the regression optimization;
   computer readable program code for causing receiving a measured signal;
   computer readable program code for causing a computer to effect selecting values for one or more members selected from the group consisting of at least one parameter, at least one range associated with the at least one parameter, and at least one resolution associated with the at least one range;
   computer readable program code for causing said computer to effect running the regression optimization using the selected values, wherein one or more simulations are run during the regression optimization, and wherein the one or more simulations are compared to the measured signal during the regression optimization;
   computer readable program code for causing said computer to effect generating regression results associated with the running of the regression optimization;
   computer readable program code for causing amid computer to effect analyzing the generated regression results; and
   computer readable program code for causing said computer to effect using the generated regression results to adjust at least one member selected from the group consisting of the at least one parameter, the at least one range, and the at least one resolution.

11. An article of manufacture comprising:
   a computer usable medium including computer readable program code embodied therein for causing setting up a regression optimization, the computer readable program code in said article of manufacture comprising:
   computer readable program coda for causing a computer to effect receiving a measured signal;
   computer readable program code for causing said computer to effect selecting values for one or more members selected from the group consisting of at least one parameter, at least one range associated with the at least one parameter, arid at least one resolution associated with the at least one range;
   computer readable program code for causing said computer to effect running the regression optimization using the selected values, wherein one or more simulations are run during the regression optimization, and wherein the one or more simulations are compared to the measured signal during the regression optimization;
   computer readable program code for causing said computer to effect generateing regression results associated with the running of the regression optimization;
   computer readable program code for causing said computer to effect analyzing the generated regression results; and
   computer readable program code for causing said computer to effect using the generated regression results to adjust at least one member selected from the group consisting of the at least one parameter, the at least one range, and the at least one resolution.

12. The computer program product of claim 10, wherein the set of measurements is associated with a grating profile, and wherein the at east one parameter includes at least one member selected from a top cd, a bottom cd, a sidewall angle, and a thickness.

13. The article of manufacture of claim 11, wherein the set of measurements is associated with a grating profile, and wherein the at least one parameter includes at least one member selected from a top cd, a bottom cd, a sidewall angle, and a thickness.

14. A computer program product for use in setting up a regression optimization, said computer program product comprising:
   a computer usable medium including computer readable program code embodied in said medium for setting up the regression optimization;
   computer readable program code for causing a computer to effect determining a first set of regression parameters;
   computer readable program code for causing said computer to effect receiving a first set of measurements associated with a first profile;
   computer readable program code for causing said computer to effect running the regression optimization on the first set of measurements to obtain a first set of resultant parameter values associated with the first profile;
   computer readable program code for causing said computer to effect storing the first set of resultant parameter values to a storage location;
   computer readable program code for causing said computer to effect receiving a second set of measurements associated with a second profile;
   computer readable program code for causing said computer to effect running the regression optimization on the second set of measurements to obtain a second set of resultant parameter values associated with the second profile; and
   computer readable program code for causing said computer to effect determining a second set of regression parameters, wherein the second set of regression parameters is associated with at least one member selected from the group consisting of the first set of resultant parameter values and the second set of resultant parameter values.

15. An article of manufacture comprising:
   a computer usable medium including computer readable program code embodied therein for causing setting up a regression optimization, the computer readable program coda in said article of manufacture comprising:
   computer readable program code for causing a computer to effect determining a first set of regression parameters;
   computer readable program code for causing said computer to effect receiving a first set of measurements associated with a first profile;
   computer readable program code for causing said computer to effect running the regression optimization on the first set of measurements to obtain a first set of resultant parameter values associated with the first profile;
   computer readable program code for causing said computer to effect storing the first set of resultant parameter value to a storage location;
   computer readable program code for causing said computer to effect receiving a second set of measurements associated with a second profile;

computer readable program code for causing said computer to effect running the regression optimization on the second set of measurements to obtain a second set of resultant parameter values associated with the second profile; and computer readable program code for causing said computer to effect determining a second set of regression parameters, wherein the second set of regression parameters is associated with at least one member selected from the group consisting of the first set of resultant parameter values and the second set of resultant parameter values.

16. A computer program product for use in setting up a regression optimization, said computer program product comprising:

a computer usable medium including computer readable program code embodied in said medium for setting up the regression optimization;

computer readable program code for causing a computer to effect determining a first set of one or more regression parameter ranges;

computer readable program code for causing said computer to effect receiving a first set of measurements associated with a first profile;

computer readable program code for causing said computer to effect running the regression optimization on the first set of measurements to obtain a first set of resultant parameter values associated with the first profile;

computer readable program code for causing said computer to effect storing the first set of resultant parameter values to a storage location;

computer readable program code for causing said computer to effect receiving a second set of measurements associated with a second profile;

computer readable program coda for causing said computer to effect running the regression optimization on the second set of measurements to obtain a second set of resultant parameter values associated with the second profile; and computer readable program code for causing said computer to effect determining a second set of one or more regression parameter ranges, wherein the second set one or more regression parameter ranges is associated with at least one member selected from the group consisting of the first set of resultant parameter values and the second set of resultant parameter values.

17. An article of manufacture comprising:

a computer usable medium including computer readable program code embodied therein for causing setting up a regression optimization, the computer readable program code in said article of manufacture comprising:

computer readable program code for causing a computer to effect determining a first met of one or more regression parameter ranges;

computer readable program code for causing said computer to effect receiving a first set of measurements associated with a first profile;

computer readable program code for causing said computer to effect running the regression optimization on the first set of measurements to obtain a first set of resultant parameter values associated with the first profile;

computer readable program code for causing said computer to effect storing the first set of resultant parameter values to a storage location;

computer readable program code for causing said computer to effect receiving a second set of measurements associated with a second profile;

computer readable program code for causing said computer to effect running the regression optimization on the second set of measurements to obtain a second set of resultant parameter values associated with the second profile; and computer readable program code for causing said computer to effect determining a second set of one or more regression parameter ranges, wherein the second set one or more regression parameter ranges is associated with at least one member selected from the group consisting of the first set of resultant parameter values and the second set of resultant parameter values.

18. A method of setting up a regression optimization, comprising:

obtaining a measured signal of a structure, wherein the measured signal is measured using an optical metrology device;

selecting a parameter from a set of parameters that characterize a profile for the structure;

selecting a range over which the parameter is to be varied;

selecting a resolution for the range;

running the regression optimization using the selected parameter, range, and resolution, wherein one or more simulations are run during the regression optimization, and wherein one or more simulations are compared to the measured signal during the regression on optimization;

obtaining regression results associated with the running of the regression optimization; and adjusting the selected range based on the regression results.

19. The method of claim 18, wherein the structure is a grating.

20. The method of claim 18, wherein the parameter includes at least one member selected from a top critical dimension (cd), a bottom cd, a sidewall angle, and a thickness.

21. The method of claim 18, wherein running the regression optimization comprises:

a) running a simulation for a set of values for the selected parameter within the selected range to generate a simulated signal;

b) comparing the simulated signal with the measured signal; and c) if the comparison in b) does not meet a goodness of fit:
storing the set of values and the simulated signal in a database; and
iterating a) and b) using another set of values for the selected parameter within the selected range and at the selected resolution.

22. The method of claim 21, further comprising:

d) before a), determining if the set of values exists in the database;

e) if the set of values does not exist in the database, performing a), b), and c); and f) if the set of values exists in the database,
i) retrieving a simulated signal corresponding to the set of values from the database;
ii) comparing the simulated signal with the measured signal; and
iii) if the comparison in ii) does not meet the goodness of fit, iterating d), e), and f) using another set of values for the selected parameter within the selected range and at the selected resolution.

23. The method of claim 22, further comprising:
determining if all value combinations for the selected parameter within the selected range at the selected resolution have been stored in the database;
if all of the value combinations have not been stored in the database, continuing to perform a) through f); and
if all of the value combinations have been stored in the database, compiling the database into a library.

24. A computer-readable storage medium containing computer executable instructions for causing a computer to set up a regression optimization, comprising instructions for:
obtaining a measured signal of a structure, wherein the measured signal is measured using an optical metrology device;
selecting a parameter from a set of parameters that characterize a profile for the structure;
selecting a range over which the parameter is to be varied;
selecting a resolution for the range;
running the regression optimization using the selected parameter, range, and resolution, wherein one or more simulations are rum during the regression optimization, sad wherein one or more simulations are compared to the measured signal during the regression optimization;
obtaining regression results associated with the running of the regression optimization; and
adjusting the selected range based on the regression results.

25. The computer-readable storage medium of claim 24, wherein the structure is a grating.

26. The computer-readable storage medium of claim 24, wherein the parameter includes at least one member selected from a top critical dimension (cd), a bottom cd, a sidewall angle, and a thickness.

27. The computer-readable storage medium of claim 24, wherein running the regression optimization comprises:

a) running a simulation for a set of values for the selected parameter within the selected range to generate a simulated signal;
b) comparing the simulated signal with the measured signal; and
c) if the comparison in b) does not meet a goodness of fit:
    storing the set of values and the simulated signal in a database; and
    iterating a) and b) using another set of values for the selected parameter within the selected range and at the selected resolution.

28. The computer-readable storage medium of claim 27, further comprising instructions for:
d) before a), determining if the set of values exists in the database;
e) if the set of values does not exist in the database, performing a), b), and c); and
f) if the set of values exist In the database,
    i) retrieving a simulated signal corresponding to the set of values from the database;
    ii) comparing th simulated signal with the measured signal; and
    iii) if the comparison in ii) does not meet the goodness of fit, iterating d), e), and f) using another set of values for the selected parameter within the selected range and at the selected resolution.

29. The computer-readable storage medium of claim 28, further comprising instructions for:
determining if all value combinations for the selected parameter within the selected range at the selected resolution have been stored in the database;
if all of the value combinations have not been stored in the database, continuing to perform a) through f); and
if all of the value combinations have been stored in the database, compiling the database into a library.

* * * * *